US00PP19697P2

(12) United States Plant Patent
Vandenberg

(10) Patent No.: US PP19,697 P2
(45) Date of Patent: Feb. 10, 2009

(54) ***CHRYSANTHEMUM* PLANT NAMED 'YOCANDLE'**

(50) Latin Name: *Chrysanthemum×morifolium*
Varietal Denomination: Yocandle

(75) Inventor: Cornelis P. Vandenberg, Fort Myers, FL (US)

(73) Assignee: Yoder Brothers, Inc, Barberton, OH (US)

( * ) Notice: Subject to any disclaimer, the term of this patent is extended or adjusted under 35 U.S.C. 154(b) by 0 days.

(21) Appl. No.: 12/011,444

(22) Filed: Jan. 25, 2008

(51) Int. Cl.
*A01H 5/00* (2006.01)

(52) U.S. Cl. ..... Plt./298
(58) Field of Classification Search ..... Plt./298
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Yocandle', characterized by its upright plant habit; dark green-colored foliage; freely and uniformly flowering habit; anemone-type inflorescences that are about 7.6 cm in diameter; attractive bronze red-colored ray florets; strong and thick peduncles; and good postproduction longevity.

3 Drawing Sheets

Botanical designation: *Chrysanthemum×morifolium.*
Cultivar denomination: 'Yocandle'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Yocandle'.

The new *Chrysanthemum* is a product of a planned breeding program conducted by the Inventor in Salinas, Calif. and Bogota, Colombia. The objective of the program is to create and develop new cut *Chrysanthemum* cultivars having numerous inflorescences with strong peduncles, good form and substance, attractive floret coloration and good postproduction longevity.

The new *Chrysanthemum* originated from a cross-pollination made by the Inventor in December, 2000, in Salinas, Calif. of a proprietary selection of *Chrysanthemum×morifolium* identified as code number T1831, not patented, as the female, or seed, parent with a proprietary selection of *Chrysanthemum×morifolium* identified as code number T3447, not patented, as the male, or pollen, parent. The new *Chrysanthemum* was discovered and selected by the Inventor as a single flowering plant within the progeny of the stated cross-pollination in a controlled environment in Bogota, Colombia in March, 2002. The selection of this plant was based on its strong peduncles, desirable ray floret color, good inflorescence form and substance and good postproduction longevity.

Asexual reproduction of the new *Chrysanthemum* by terminal cuttings in a controlled environment in Bogota, Colombia since May, 2002, has shown that the unique features of this new *Chrysanthemum* are stable and reproduced true to type in successive generations.

SUMMARY OF THE INVENTION

Plants of the cultivar Yocandle have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yocandle'. These characteristics in combination distinguish 'Yocandle' as a new and distinct cultivar of *Chrysanthemum:*

1. Upright plant habit.
2. Dark green-colored foliage.
3. Freely and uniformly flowering habit.
4. Anemone-type inflorescences that are about 7.6 cm in diameter.
5. Attractive bronze red-colored ray florets.
6. Response time about 63 days.
7. Strong and thick peduncles.
8. Good postproduction longevity with inflorescences and foliage maintaining good substance and color for about two weeks in an interior environment.

Plants of the new *Chrysanthemum* differ from plants of the female parent selection in the following characteristics:

1. Plants of the new *Chrysanthemum* are shorter than plants of the female parent selection.
2. Plants of the new *Chrysanthemum* flower about two to three days later than plants of the female parent selection.
3. Plants of the new *Chrysanthemum* produce more inflorescences per flowering stem than plants of the female parent selection.
4. Plants of the new *Chrysanthemum* have anemone-type inflorescences whereas plants of the female parent selection have daisy-type inflorescences.
5. Inflorescences of plants of the new *Chrysanthemum* have bronze red-colored ray florets whereas inflorescences of plants of the female parent selection have red purple-colored ray florets.

Plants of the new *Chrysanthemum* differ from plants of the male parent selection in the following characteristics:

1. Plants of the new *Chrysanthemum* are slightly shorter than plants of the male parent selection.

2. Plants of the new *Chrysanthemum* flower about two days later than plants of the male parent selection.
3. Plants of the new *Chrysanthemum* produce more inflorescences per flowering stem than plants of the male parent selection.
4. Plants of the new *Chrysanthemum* have anemone-type inflorescences whereas plants of the male parent selection have daisy-type inflorescences.
5. Inflorescences of plants of the new *Chrysanthemum* have bronze red-colored ray florets whereas inflorescences of plants of the male parent selection have orange-colored ray florets.

Plants of the new *Chrysanthemum* can be compared to plants of the *Chrysanthemum* cultivar Omaha, disclosed in U.S. Plant Pat. No. 10,197. In side-by-side comparisons conducted in Bogota, Colombia, plants of the new *Chrysanthemum* differed from plants of the cultivar Omaha in the following characteristics:

1. Plants of the new *Chrysanthemum* flowered about one week earlier than plants of the cultivar Omaha.
2. Plants of the new *Chrysanthemum* produced more inflorescences per flowering stem than plants of the cultivar Omaha.
3. Plants of the new *Chrysanthemum* had shorter peduncles than plants of the cultivar Omaha.
4. Inflorescences of plants of the new *Chrysanthemum* had bronze red-colored ray florets whereas inflorescences of plants of the cultivar Omaha had dark red-colored ray florets.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering stem of 'Yocandle'.

The photograph on the second sheet is a close-up view of typical developing inflorescences of 'Yocandle'.

The photograph on the third sheet is a close-up view of a typical fully developed inflorescence of 'Yocandle'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bogota, Colombia during the summer and autumn in a polyethylene-covered greenhouse and under conditions and practices which approximate those generally used in commercial *Chrysanthemum* production. During the production of the cut flowers, day temperatures ranged from 20° C. to 25° C., night temperatures ranged from 4° C. to 9° C. and light levels ranged from 3,000 to 4,000 foot-candles. Measurements and numerical values represent averages for typical flowering plants. The photographs and measurements were taken from flowering stems of plants that were about three months old.

BOTANICAL CLASSIFICATION *Chrysanthemum×morifolium* cultivar Yocandle.

Parentage:

*Female, or seed, parent.*—Proprietary selection of *Chrysanthemum×morifolium* identified as code number T1831, not patented.

*Male, or pollen, parent.*—Proprietary selection of *Chrysanthemum×morifolium* identified as code number T3447, not patented.

PROPAGATION:

*Type.*—Terminal vegetative cuttings.

*Time to initiate roots.*—About 10 to 14 days with soil temperatures of about 18° C. to 21° C.

*Root description.*—Fine, fibrous; white in color.

*Rooting habit.*—Freely branching.

Plant description:

*Appearance.*—Herbaceous anemone-type cut flower.

*Flowering stem descriptions.*—Aspect: Erect. Length: About 91 cm. Spray diameter: About 15 cm. Stem diameter: About 8 mm. Internode length: About 3.75 cm. Texture: Pubescent; longitudinally ridged. Color: Close to 146A.

*Foliage description.*—Arrangement: Alternate; simple. Length: About 9.2 cm. Width: About 6.4 cm. Apex: Cuspidate. Base: Truncate. Margin: Palmately lobed; irregularly serrate; sinuses mostly parallel. Texture, upper and lower surfaces: Pubescent; veins prominent on lower surface. Color: Developing and fully expanded foliage, upper surface: Darker than 147A; venation, close to 147B. Developing and fully expanded foliage, lower surface: Close to 147A to more green than 147A; venation, close to 147B. Petiole: Length: About 2.2 cm. Diameter: About 4 mm. Texture, upper and lower surfaces: Pubescent. Color, upper surface: Center, close to 147C; towards the margins, close to 147B. Color, lower surface: Close to 147C.

Inflorescence description:

*Appearance.*—Anemone-type inflorescence form with elongated oblong-shaped ray florets. Inflorescences borne on terminals, arising from leaf axils. Ray and disc florets develop acropetally on a capitulum. Uniform flowering habit.

*Fragrance.*—Moderate; herbaceous.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 63 days later.

*Postproduction longevity.*—In an interior environment, inflorescences and foliage will maintain good color and substance for about two weeks in an interior environment.

*Quantity of inflorescences.*—Freely flowering habit, about eight inflorescences per stem develop.

*Inflorescence size.*—Diameter: About 7.6 cm. Depth (height): About 1.8 cm. Disc diameter: Enlarged; about 3.4 cm. Receptacle diameter: About 9 mm. Receptacle height: About 8 mm.

*Inflorescence buds.*—Shape: Oblate. Height: About 1 cm. Diameter: About 8 mm. Color: More green than 147A.

*Ray florets.*—Shape: Elongated oblong. Surface: Concave. Aspect: Initially incurved, with development, about 90° from vertical and eventually reflexing. Length: About 3.75 cm. Width: About 9 mm. Apex: Acute, rounded or emarginate. Base: Fused. Corolla tube length: About 7.5 mm. Corolla tube diameter, at base: About 1.5 mm. Texture: Smooth, glabrous; velvety; longitudinally ridged. Number of ray florets per inflorescence: About 128 arranged in about five or six whorls. Color: When opening and fully opened, upper surface: Close to 9A heavily overlaid with between 46A and 53A. When opening, lower surface: Close to 6B underlain with close to 53A.

*Disc florets.*—Shape: Tubular, enlarged; typically five-parted. Length: About 1.5 cm. Diameter: About 1.5 mm. Texture, outer and inner surfaces: Smooth, glabrous. Number of disc florets per inflorescence: About 165 in numerous whorls. Color, immature, outer and inner surfaces: Apex and mid-section: Close to 154A. Base: Close to 155D. Color, mature, outer surface: Apex and mid-section: Close to 9A to 9B faintly underlain with close to 53A. Base: Close to 155D. Color, mature, inner surface: Apex: Close to 46A. Mid-section: Close to 9A. Base: Close to 155D.

*Phyllaries.*—Quantity per inflorescence/arrangement: About 24 arranged in about three whorls. Length: About 1 cm. Width: About 4 mm. Shape: Lanceolate. Apex: Acute. Base: Truncate. Margin: Entire. Texture, upper surface: Smooth, glabrous. Texture, lower surface: Pubescent. Color, upper surface: More green than 146A. Color, lower surface: More green than 147A.

*Peduncles.*—Length, terminal peduncle: About 9.5 cm. Length, fourth peduncle: About 12.5 cm. Length, seventh peduncle: About 14 cm. Diameter, terminal peduncle: About 3.5 mm. Angle: About 20° to 30° from vertical. Strength: Strong. Texture: Pubescent; longitudinally ridged. Color: Close to 146A.

*Reproductive organs.*—Androecium: Filament length: About 4 mm. Filament color: Close to 155D. Anther length: About 1 mm. Anther shape: Narrowly oblong. Anther color: Close to 15A. Pollen amount: None observed. Gynoecium: Pistil length: About 6 mm. Stigma shape: Bi-parted. Stigma color: Close to 12A. Style length: About 4 mm. Style color: Close to 145A. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

What is claimed is:

1. A new and distinct *Chrysanthemum* plant named 'Yocandle' as illustrated and described.

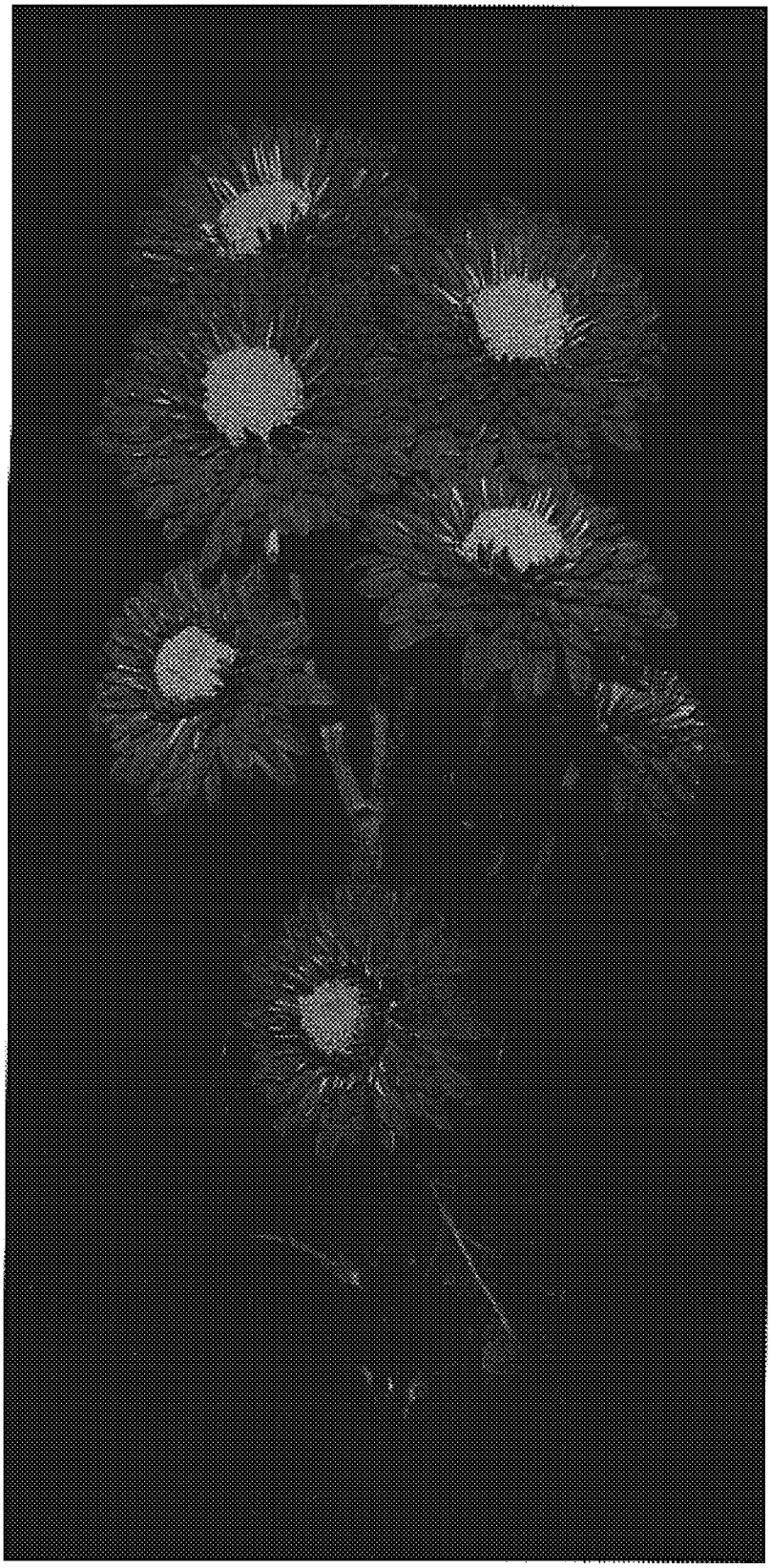

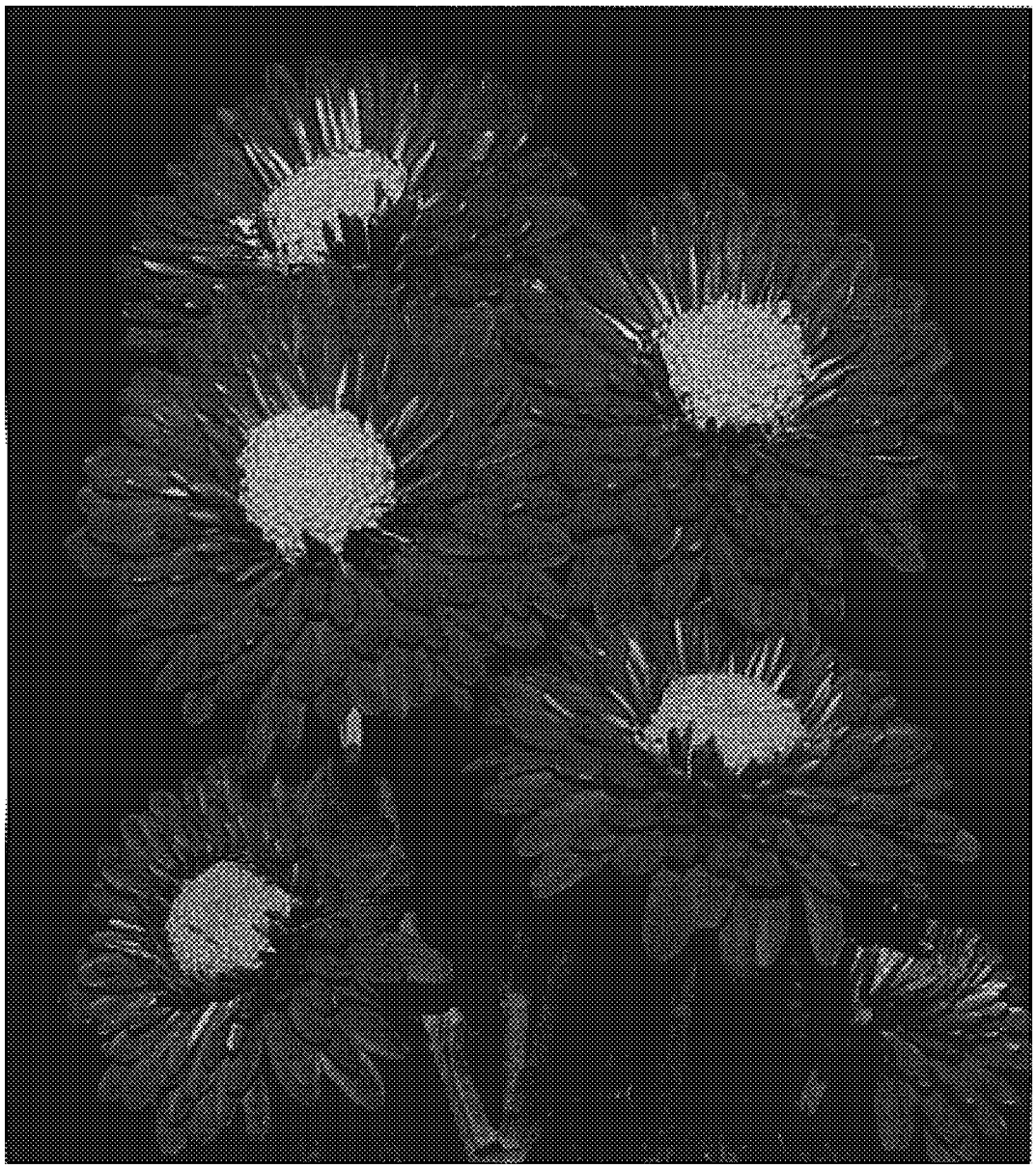

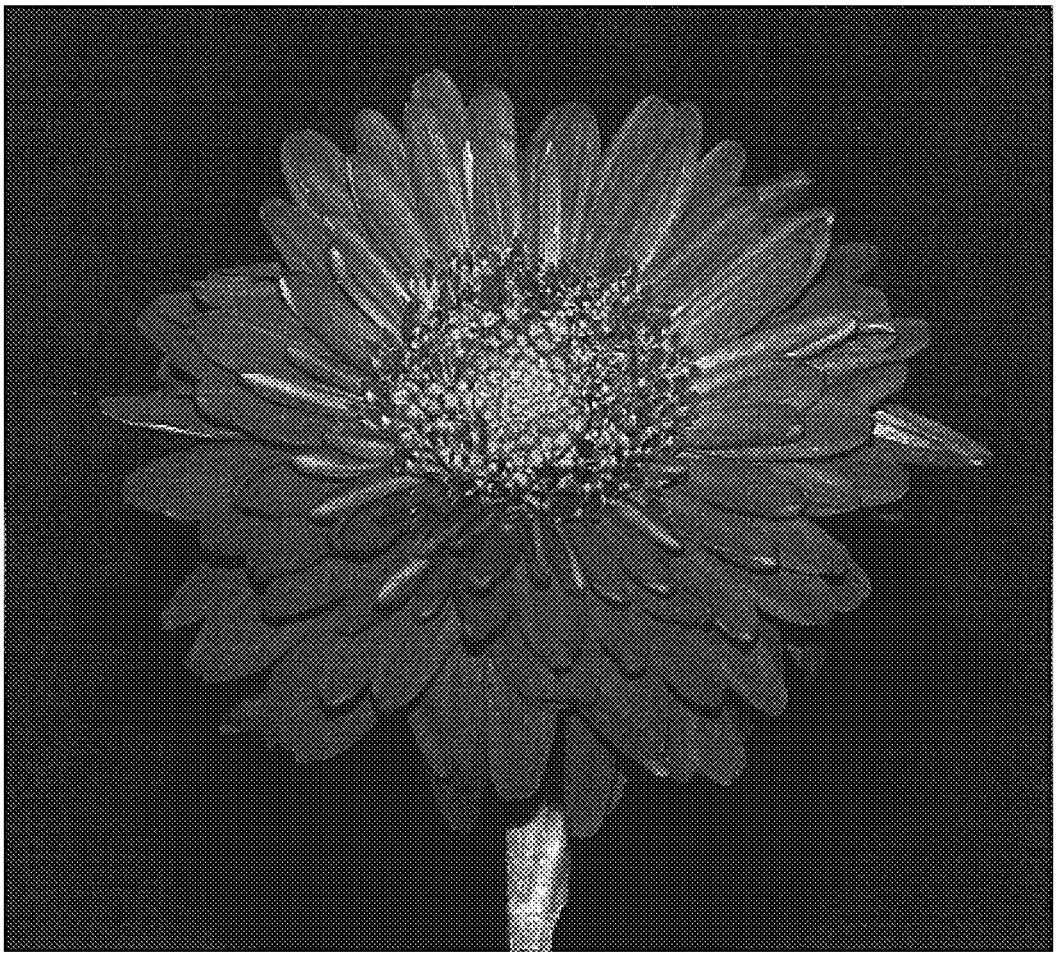

* * * * *